(12) United States Patent
Njemanze

(10) Patent No.: US 6,547,737 B2
(45) Date of Patent: Apr. 15, 2003

(54) INTELLIGENT TRANSCRANIAL DOPPLER PROBE

(76) Inventor: Philip Chidi Njemanze, P.O. Box 302 No. 1 Uratta Road, Owerri, Imo (NG)

( * ) Notice: Subject to any disclaimer, the term of this patent is extended or adjusted under 35 U.S.C. 154(b) by 0 days.

(21) Appl. No.: 10/098,064

(22) Filed: Mar. 15, 2002

(65) Prior Publication Data

US 2002/0103436 A1 Aug. 1, 2002

Related U.S. Application Data

(63) Continuation-in-part of application No. 09/483,764, filed on Jan. 14, 2000, now abandoned.

(51) Int. Cl.[7] .................................................. A61B 5/00
(52) U.S. Cl. ........................... 600/454; 607/23; 607/24; 600/457
(58) Field of Search ................................. 600/454, 453, 600/437, 452, 426, 457, 459, 443, 422, 455, 462, 465, 467, 480, 486; 128/202.11; 607/17–19, 23, 24; 604/891, 500, 66

(56) References Cited

U.S. PATENT DOCUMENTS

| | | | | |
|---|---|---|---|---|
| 5,058,592 A | * | 10/1991 | Whisler | 600/453 |
| 5,070,880 A | * | 12/1991 | Gomez et al. | 600/452 |
| 5,121,744 A | * | 6/1992 | Njemanze | 128/202.11 |
| 5,390,675 A | * | 2/1995 | Sheehan et al. | 600/453 |
| 5,891,034 A | * | 4/1999 | Bucholz | 600/426 |
| 6,261,231 B1 | * | 7/2001 | Damphousse et al. | 600/437 |
| 6,468,219 B1 | * | 10/2002 | Njemanze | 600/454 |

* cited by examiner

Primary Examiner—Marvin M. Lateef
Assistant Examiner—Ruby Jain

(57) ABSTRACT

A system for automatic manipulation of a transcranial Doppler probe device designed for placement on a patient's head comprising a bi-temporal probe hanger, a cylindrical probe housing having an inner electrical wiring, an ultrasound transducer with cable affixed on the probe cylindrical base having a coil, said probe cylindrical base placed within the cylindrical probe housing, a spring system affixed to provide perpendicular pressure on the probe cylindrical base, a system of roller balls, a locking system to affix the cylindrical probe housing to the frame of the bi-temporal probe hanger, a system software program and microprocessor for controlling the probe position, and a removable handle attached to the said probe cylindrical base. The system software 'learns' probe angulations after initial manual manipulations and then performs cerebral vessel insonation using electromotive force independent of operator.

20 Claims, 8 Drawing Sheets

INTELLIGENT TRANSCRANIAL DOPPLER PROBE

CROSS-REFERENCE TO RELATED APPLICATION

Continuation-in-part of Ser. No. 09/483,764, Jan. 14, 2000, abandoned.

REFENCES CITED

U.S. Patent Documents

| U.S. PATENT DOCUMENTS | | | |
|---|---|---|---|
| US-5058592 | 10-1991 | Whisler | 12/662.03 |
| US-5070880 | 12-1991 | Gomez et al. | 128/661 |
| US-5390675 | 02-1995 | Sheenhan et al. | 128/661.07 |
| US-6261231.B1 | 07-2001 | Damphousse et al. | 600/437 |
| US-5121744 | 06-1992 | Njemanze | 128/202.11 |

OTHER PUBLICATIONS

Aaslid R. Transcranial Doppler Sonography. Springer, Wien, pages 39–50, 1989.

Fullér R. Advances in soft computing: introduction to neuro-fuzzy systems. Physica-Verlag, Berlin, 2000.

Nelkon M. and Parker P. Advanced Physics. Heinemann educational books Ltd, London, pages 895–966, 1971.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

The present invention relates to transcranial Doppler probe device in general and in particular to a device for mounting transcranial Doppler probes on a patient's head and automatically insonating the cerebral vessels.

Transcranial Doppler (TCD) Sonography is an imaging technique that uses Doppler ultrasound principle to measure cerebral blood flow in basal cerebral arteries. The basic principles for common clinical applications are detailed in a book edited by Aaslid R, entitled "Transcranial Doppler Sonography" and published by Springer, Vienna, dated 1989, on pages 39 through 50. However, one major problem that limits the use of TCD for long-term clinical and ambulatory monitoring in medical practice and research is the positioning of the transcranial Doppler ultrasound transducer to ensure steady ultrasound signals. In clinical practice the operator typically locates the Doppler signal by manipulating the probe over the appropriate cranial temporal acoustic windows. Once the TCD signals are found the operator fixes the probe in position and optimizes the signal quality before locking it at the best probe-to-vessel angle. The probe is then held in place by a stabilization device usually an elastic headband. Slight head movements could change the probe-to-vessel angle and cause the loss of TCD signals. This will necessitate manipulating the probe to locate the Doppler signals again by a trained operator, leading to cumbersomeness, long examination time and disruption of data acquisition protocols.

Prior art of currently in use TCD probe assemblies employ mechanisms that lock the ultrasound transducer in place and means to manually adjust the angulation of the TCD probe. U.S. Pat. No. 5,390,675 disclosed a method and apparatus comprising a TCD probe assembly which includes a TCD transducer, a pedastal, means for adjusting the angulation of the TCD probe in the pedastal and means for securing the pedastal to a patient's head. However, patent '675 is operator dependent incase of motion artifacts (such as coughing, yawning, biting etc). It has previously been suggested to provide a TCD probe fixation that allows continuous TCD monitoring. U.S. Pat. No. 5,070,880 discloses a probe housing stabilization device for supporting a transcranial Doppler probe against the temporal bone of the head. The device employs a generally planar, rigid member having an opening therein. The member has perforations onto which an adhesive is applied to secure it in place and the opening receives the probe thereby positioning it in place adjacent on the temporal bone. The '880 patent provides a rigid device and again lacks the flexibility of self-regulation in case of motion artifacts. U.S. Pat. No. 6,261,231 B1 discloses a hands-free ultrasound probe holder with a receptacle comprising of probe securing means, however, does not offer automatic probe position and self-regulation. U.S. Pat. No. 5,058,592 discloses an adjustable mountable TCD probe device that incorporates a Velcro fastening means to provide support and an infinite number of fastening positions. The device of '592 patent again lacks flexibility of automatic probe repositioning and self-regulation incase of shifts induced by motion artifacts. There have been attempts to determine the position of a probe relative to the body and means of adjusting the position to correct for errors responsive to a direct representation of the angular probe position. For example, U.S. Pat. No. 5,891,034 discloses a system for indicating the position of a surgical probe in the x, y, and z directions. The probe is rotated and tilted using information from a computer analysis to determine the body position. However, similar limitations as mentioned above apply to the '034 patent. U.S. Pat. No. 5,121,744 illustrated a transcranial Doppler probe incorporated into a pilot or astronaut helmet that uses a motorized device to locate cerebral vessels using the three orthogonal coordinates. However, the '744 patent involves a relatively heavier apparatus not applicable in everyday conditions and may also lack the required level of automated responsiveness necessary for involuntary motion induced artifacts.

There remains, therefore a need for a TCD probe system which provides automatically adjustable probe positions as effective substitute to manual probe repositioning in case of shifts induced by motion artifacts, and effective stabilization when optimized signals are obtained with feedback loops in a self-regulatory manner driven by an artificial intelligent system. In other words, there is required an artificial intelligent transcranial Doppler (i-TCD) probe for probe positioning in an automatic self regulating manner that is operator independent after the initial setup.

SUMMARY OF THE INVENTION

The principal objects of the present invention are a method and apparatus comprising a i-TCD probe assembly which includes a TCD transducer, bi-temporal probe hanger, cylindrical probe housing with inner wiring, probe cylindrical base with coil, probe roller balls, spring system, a removable handle and software program for adjusting the angulation of the TCD probe and a microprocessor operatively connected to the transcranial Doppler device.

The bi-temporal probe hanger is designed to allow the insertion of both probes therein into a hole provided above the temporal acoustic windows above the zygomatic arch.

The hanger rests on the center of the head, the mastoid bone and the zygomatic arch from both sides, providing a support base on bone surfaces that do not have significant mobility of overlying skin and are not affected by involuntary movement artifacts induced by coughing, jaw movement etc. The hole into which the TCD probe is inserted is modified such that the cylindrical probe housing adapts to the entire range of the space overlying the posterior, middle and anterior temporal acoustic windows with the flexibility to select the best position for insonation. The TCD transducer is affixed to a probe cylindrical base with coil that in turn is inserted into a cylindrical probe housing with inner wiring. The inner wiring provides a means to generate electromotive force for angulations of the probe and also to read the position of the probe within the housing. The latter is determined using the principle of electromagnetic induction arising between the inner wiring of the housing and the coil on the probe cylindrical base. The principles of electromagnetic induction are described in basic physics textbooks such as that by Nelkon M. and Parker P. titled "Advanced Physics" published by Heinemann educational books Ltd, London, pages 895–966, 1971. The transducer cable is affixed on the air-filled inner probe cylindrical base. The probe roller balls provide means for increased degree of freedom of movement of the probe in all three x, y, and z planes. The perpendicular spring system is fitted to the probe cylindrical base for providing a force perpendicular to a patient's head in order to improve the coupling of the probe to the skin. A lever system is derived comprising the lever as the roller balls balancing the weights of the transducer and the perpendicular pressure from the skin on one hand and the probe cylindrical base with the transducer cable and the perpendicular force from the spring system on the other, with the balance tilted in any desired direction by application of electromotive force on a set of inner wiring in the cylindrical probe housing. A software program is provided for setting the desired angulations of the probe. A removable handle is fitted to the probe cylindrical base for manually adjusting the angulations of the probe in order to 'teach' the software program to 'learn' the multiplicity of positions to find the cerebral vessels and also to select the optimal position to set threshold values for the Doppler and spectral signals. The set threshold values are used in a feedback loop to optimize the probe position.

DESCRITPTION OF THE PREFERRED EMBODIMENTS

As used herein, the "patient" is the object to be scanned using transcranial Doppler ultrasonography specifically insonating of the patient's head for diagnostic, research or even therapeutic purposes.

Figure 1:
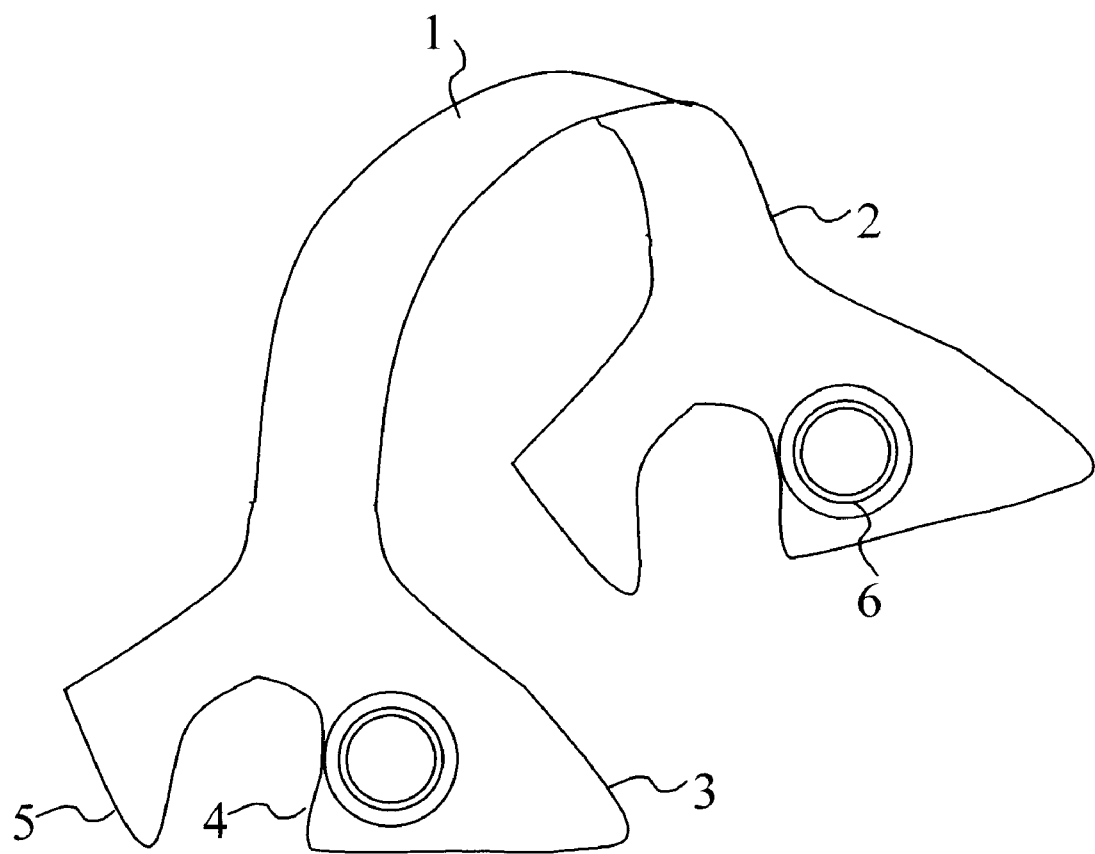
FIG. 1 is a diagram of the bi-temporal probe hanger.

Referring to FIG. 1, there is shown a bi-temporal probe hanger of one embodiment of the present invention. The probe hanger has a central arm 1 that suspends the two temporal arms 2 on the center of the head. Each temporal arm 2 has an anterior end 3 that rests on the zygomatic arch, a middle part, which has a hole 6 provided for the probe and an auricular pouch 4 that circumvents the ear lobe and the posterior part referred to as the mastoid base 5 and rests on the mastoid process. The central arm 1 and all three parts of the temporal arms 3, 4, and 5 lie on bone surfaces with minimal skin mobility including during involuntary movements such as coughing, sneezing, yawning etc. A hole 6 is provided for the cylindrical probe housing adjacent to the temporal acoustic window. The operator in one modification of the present invention could adjustably fit the probe housing to the anterior, middle and posterior temporal acoustic windows. The material of the hanger could be made of a lightweight thermoplastic with considerable flexibility to accommodate different head sizes. In one modification of the present invention the central arm could be made adjustable so as to accommodate a variety of head sizes.

Figure 2:
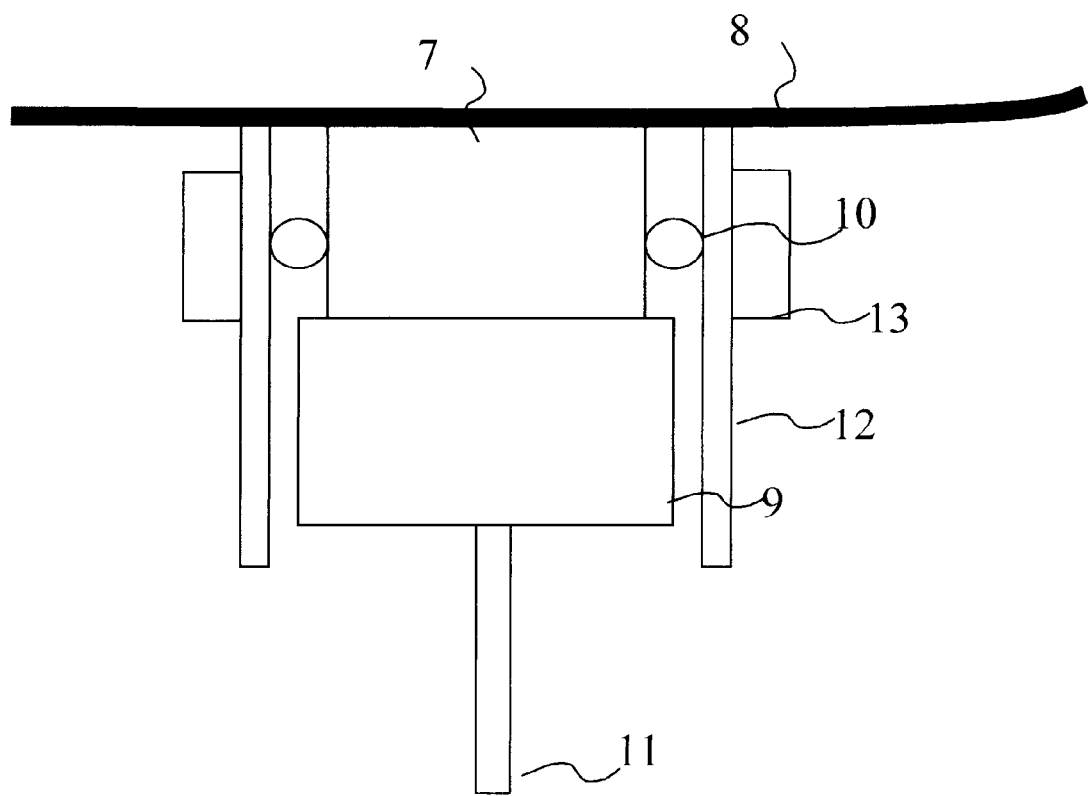
FIG. 2 is a cross-sectional view of the parts assembled on the skin of the temporal bone.

Referring now to FIG. 2, there is shown a cross-sectional diagram of the probe housing. The ultrasound probe 7 is placed on the skin overlying the temporal bone 8. The ultrasound gel is placed on the skin to facilitate acoustic coupling of the probe to the skin. The ultrasound transducer is affixed to a probe cylindrical base 9, which is an empty air-filled space designed to attenuate backward propagation of the ultrasound signal. The walls of the transducer roll on balls 10 to allow unlimited degree of freedom of movement including when using the handle 11 or electromotive force for angulations of the probe within the outer cylindrical probe housing 12. The handle 11 is used to 'teach' the system the different possibilities of probe angulations. The roller balls 10 can be electro-magnetized to lock in position using electromotive force from the inner wiring 15 (see FIG. 3) of the outer cylindrical probe housing 12. The entire housing is affixed in position to the frame of the bi-temporal probe hanger by an external locking system 13.

Figure 3:
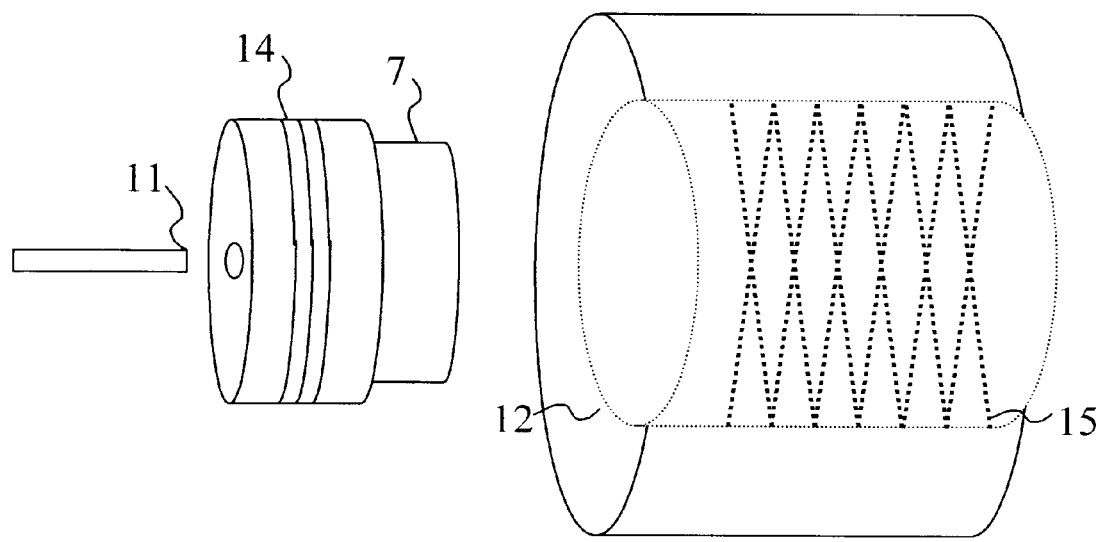
FIG. 3 is an exploded view of the elements of the device of the present invention and their assembly.
Figure 3:
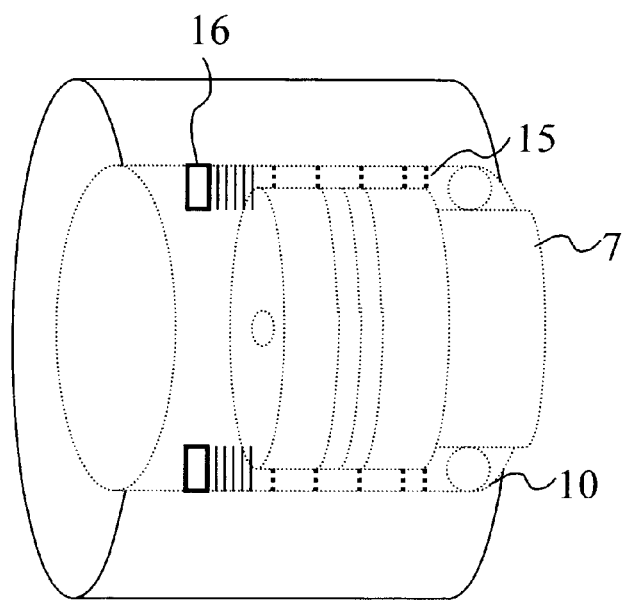

Referring now to FIG. 3, there is shown an exploded view of the elements of the probe housing in detail. The ultrasound transducer is mounted on a probe cylindrical base 9 having an outer coil 14 through which electrical voltage and electromotive force can be applied to cause deviation of the probe relative to the inner wiring 15 of the outer cylindrical probe housing 12. A spring system 16 provides the perpendicular force to improve probe-to-skin coupling along with the ultrasonic gel. A system of lever equilibrium is established between the spring system and then roller balls such that only a slight electromotive force is required to cause tilting of the probe in the desired direction.

Figure 4:
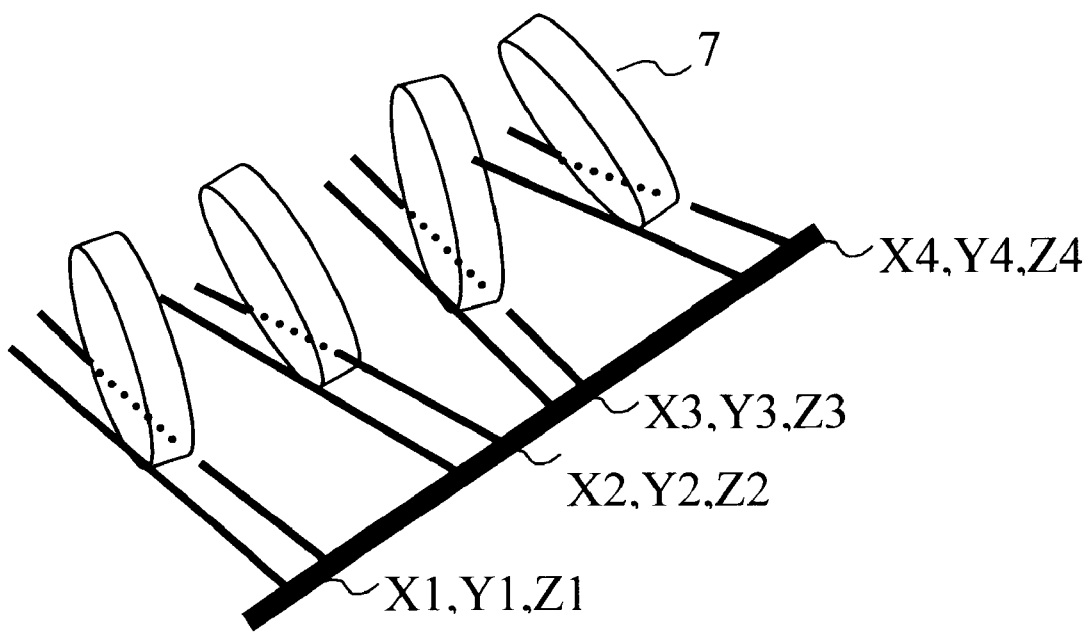
FIG. 4 illustrates the different coordinate positions of the ultrasound transducer.

Referring now to FIG. 4, there is shown a variety of directions of tilt of the probe 7 along the three orthogonal coordinates x, y and z.

Figure 5:
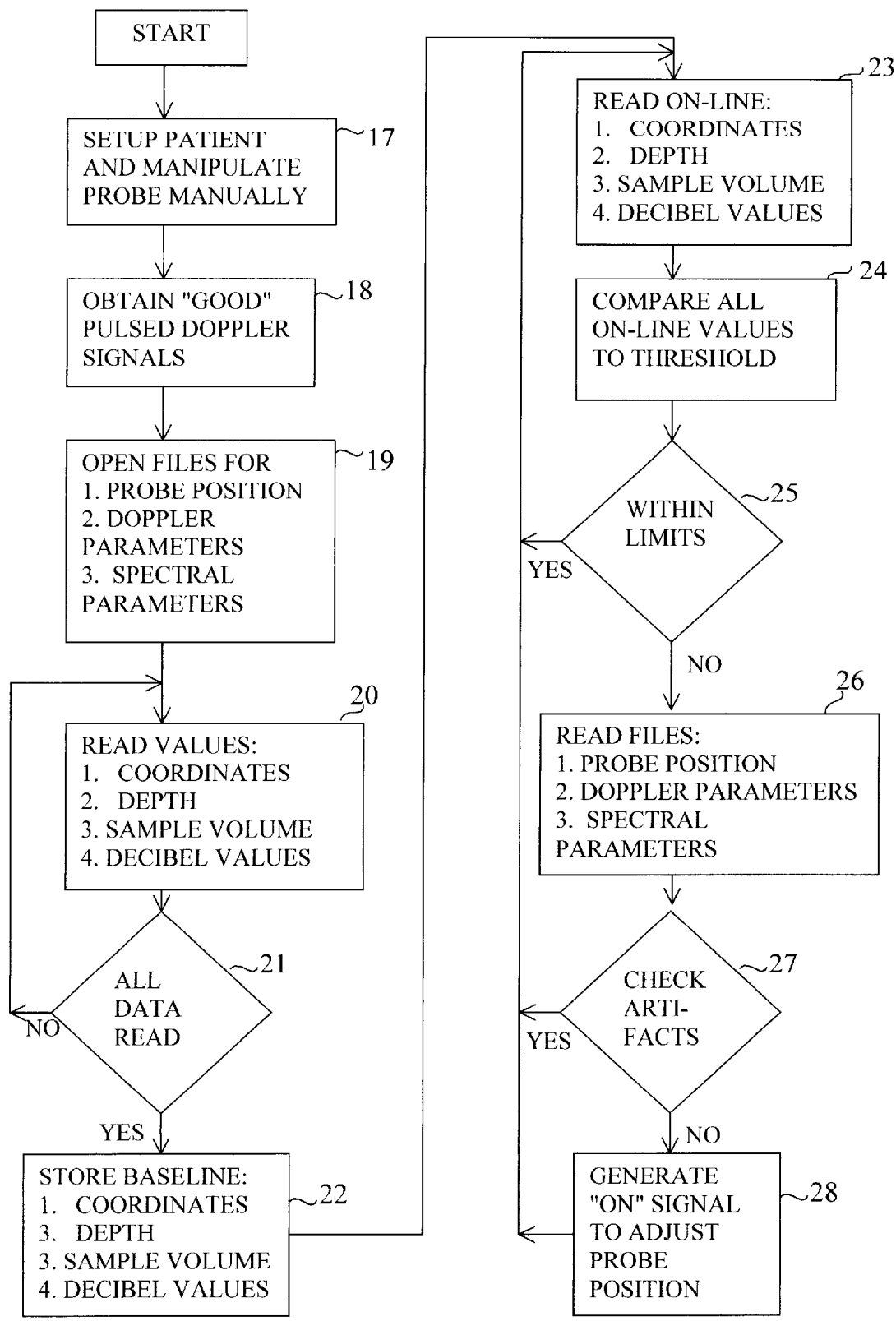
FIG. 5 is a program flow chart of function of the microprocessor of the present invention.

Referring now to FIG. 5, there is shown a flow chart of the operation of the present invention. The patient is setup in sitting or lying position as desired by the operator and the bi-temporal probe hanger placed on the head and the temporal arms positioned on both sides of the temporal bone above the zygomatic arch. The probe handle is used to manipulate the probe 17. Once "good" pulsed Doppler signals are obtained 18 the program of the control microprocessor is activated to register the probe position 19. The Doppler parameters and spectral parameters are also recorded 19. The values of the determined coordinates, depth, sample volume and decibel values are read 20, if not all are read the step is repeated 21. If yes, the program proceeds to store the determined parameters as baseline or optimal values for coordinates, depth, sample volume, and decibel values 22 in the files. The system reads on-line values for coordinates, depth, sample volume and decibel values 23 and compares the read values to set threshold values 24, if within the limits, it continues reading on-line values 25, if not, it reads the initial files of probe position containing the different values of possible coordinates, and the Doppler and spectral parameters obtained at these probe positions 26. The system checks artifacts for momentary events such as involuntary motion (such as cough, sneezing or yawning) induced artifacts that restores to steady state in a short duration before reading on-line values 27, if not, the system generates an "on" signal to adjust the probe position 28 using electromotive force. The on-line values are then read repeatedly 23. The system could automatically maintain a constant probe position by applying the appropriate electromotive force to immobilize the roller balls.

Figure 6:
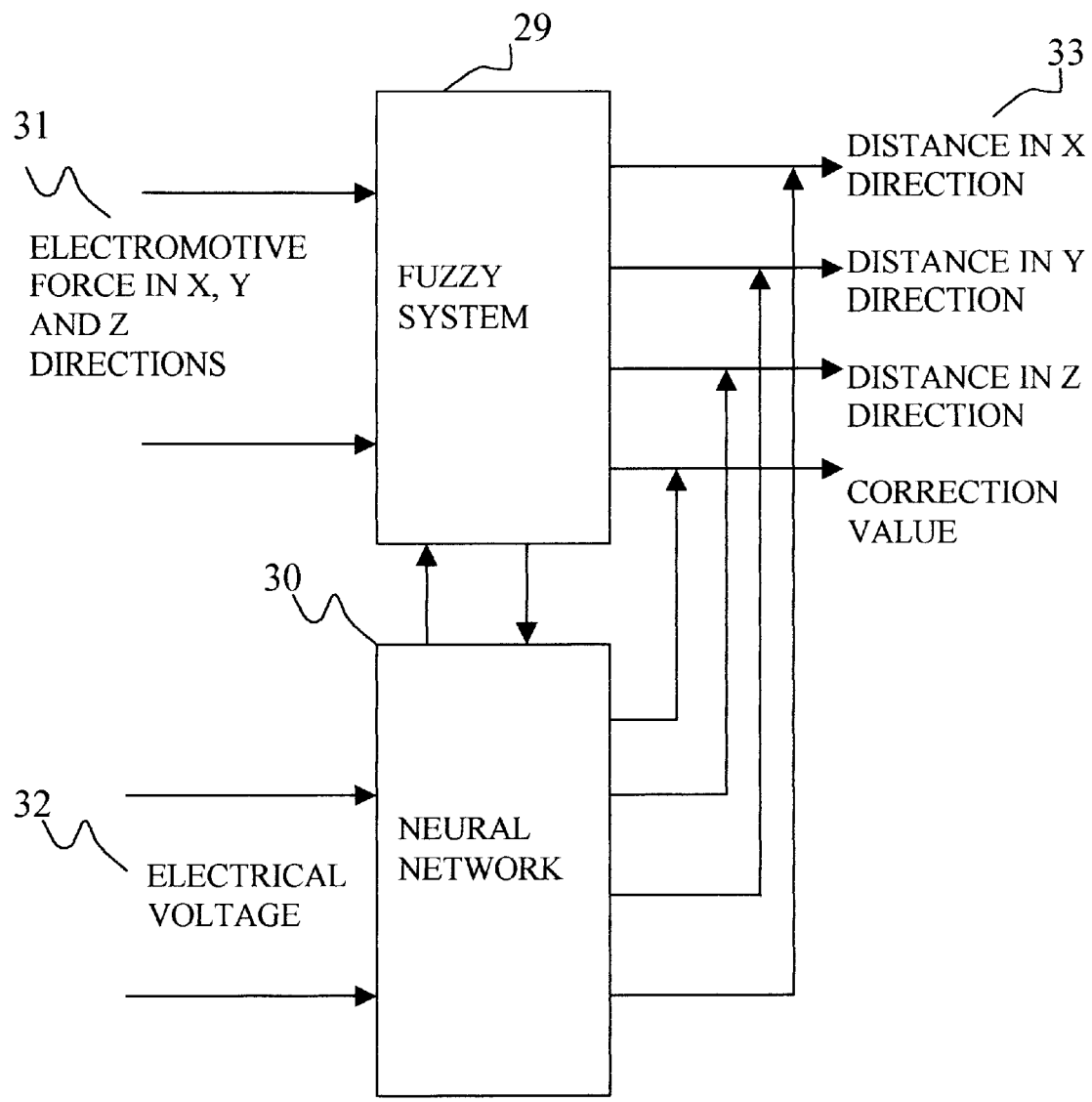
FIG. 6 is a schematic of fizzy and neural network control of probe repositioning according to the present invention.

Referring now to FIG. 6, there is shown one way to adjust the probe-vessel angle by combined fuzzy system and neural network connected serially. The probe is initially rotated manually to set the desired Doppler signal quality using the handle 11. The computer detects on the wiring 15 of the cylindrical probe housing the strength of the electromotive force generated from the inner probe cylindrical base with coil 14. First, the distance in all three x, y and z coordinates are calculated by a fuzzy system 29 using the ratios of the sensed strength of the electromotive force to electrical voltage applied to the neural network to build a fuzzy database which stores and retrieves information on probe position. Neural network 30 using the ratio between the electromotive force 31 and applied electrical voltage 32 to compute the required correcting value for distance in all three coordinates 33 and thus the effective strength of the electromotive force to be applied for probe repositioning. The desired effect of determining position and repositioning of the probe is achieved using electrical voltage applied alternately to the inner wiring of the probe cylindrical housing and the coil at probe cylindrical base using the principle of induction and electromagnetism mentioned above. In other words, the electromotive force values are used in neural networks to design membership functions of fuzzy system that are employed for decision-making algorithms for controlling the probe position. The neural network's internal connections and synaptic weights are in turn initialized using the knowledge of the fuzzy logic system; it learns by back propagation learning and changes its symbolic representation accordingly. This representation is then returned to a fuzzy logic representation, and the system has acquired knowledge. The system can make probe angulations based on the knowledge it has acquired. Details of fuzzy and neural network approach will appear obvious to anyone skilled in the art as described in a book by Fullér R. (Fullér R. Advances in soft computing: introduction to neuro-fuzzy systems. Physica-Verlag 2000.). The system has the capacity to store the learned data in the computer memory under a specified file name for the patient. This can be repeatedly accessed, as the patient requires insonation. After the initial learning, subsequently the device uses its knowledge base to find the probe-to-vessel angle required for insonation without the input of the operator provided the bi-temporal probe hanger is placed according to the same landmarks each time by the patient. Thus the device henceforth does not require a specially trained operator for insonation.

Figure 7:
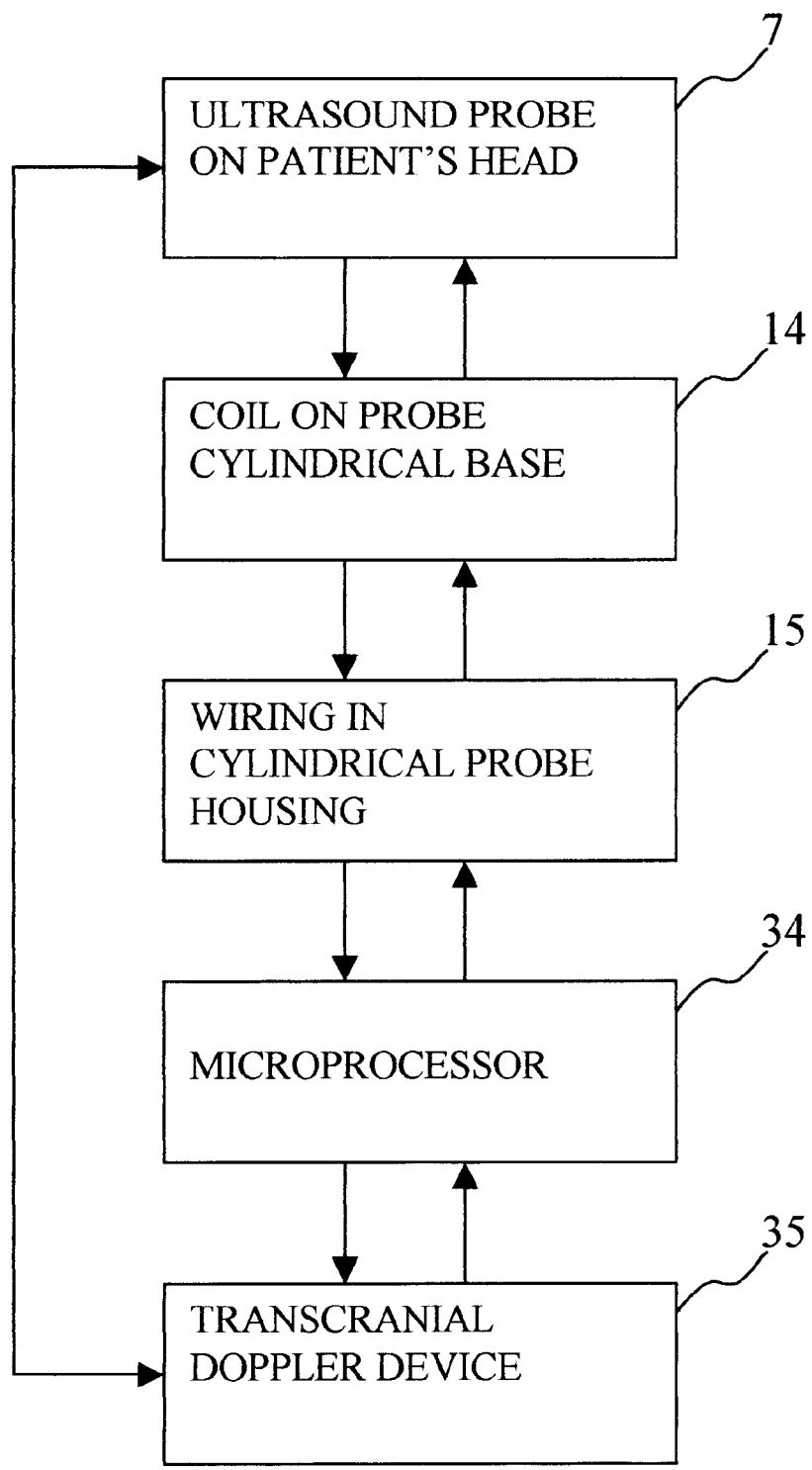
FIG. 7 is a schematic of the operational connection of the device of the present invention.

Referring to FIG. 7, there is shown a schematic diagram of the system with ultrasound probe placed on patient head 7. The probe position can be altered by means of electromotive force applied on a coil on the probe cylindrical base 14 using electrical voltage applied to the wiring in the cylindrical probe housing 15. The program of the microprocessor 34 incorporated within the transcranial Doppler equipment 35 alters the probe position and is connected to the probe via the transducer cable 36 (see FIG. 8).

Figure 8:
FIG. 8 is a side view of the device of the present invention placed on head of a patient.

Referring to FIG. 8, there is shown a side view of the device placed on a patient's head. The transducer cable 36 is attached to the probe 7 and passes from within the probe cylindrical housing 12 to connect the device to the transcranial Doppler equipment 35.

What I claim as my invention are:

1. A system for automatic manipulation of a transcranial Doppler probe device designed for placement on a patient's head comprising:
   a bi-temporal probe hanger with two temporal arms;
   a cylindrical probe housing mounted on a hole on each arm of the said bi-temporal probe hanger wherein said cylindrical probe housing having an inner electrical wiring;
   an ultrasound transducer with cable operatively connected to the transcranial Doppler device and affixed on the probe cylindrical base wherein said probe cylindrical base inserted in the said cylindrical probe housing and said probe cylindrical base having a coil;
   a spring system affixed to the said cylindrical probe housing and providing perpendicular pressure on the probe cylindrical base;
   a system of roller balls within the said probe cylindrical housing;
   a locking system to affix the cylindrical probe housing to the frame of the bi-temporal probe hanger above an acoustic window;
   a system software program;
   a microprocessor for controlling an probe position and operatively connected to the transcranial Doppler device and the inner wiring of the cylindrical probe housing and coil at the probe cylindrical base; and
   a removable handle attached to the said probe cylindrical base.

2. A system according to claim 1, wherein the cylindrical probe housing comprises an inner wiring and the probe cylindrical base comprises a coil wherein electrical voltage is applied to generate an inner electromotive force.

3. A system according to claim 2, wherein the electromotive force is controlled by the microprocessor using system software.

4. A system according to claim 3, wherein the software program uses the electromotive force in the inner wiring of the cylindrical probe housing to provide automated determination of the probe position.

5. A system according to claim 4, wherein the software program uses the electromotive force and spectral parameters in a servo feedback mechanism for automatic angulations of the probe within the cylindrical probe housing.

6. A system according to claim 5, wherein the electromotive force is used by a neuro-fuzzy system for probe angulations.

7. A system according to claim 6, wherein the electromotive force is generated during movement of a removable handle means for manually creating an data set for angulations of the probe, said data set used subsequently by the neuro-fuzzy system.

8. A system according to claim 7, wherein the electromotive force is used to automatically generate movement data, and said movement data comprising direction and distance of motion related artifacts and providing said movement data for probe angulations independent of an operator.

9. A system according to claim 8, wherein the electromotive force is used to tilt an balance in a lever system comprising perpendicular spring system and roller balls.

10. A system according to claim 9, wherein the spring system is used to provide perpendicular force on the probe cylindrical base to improve an coupling of the transducer to the skin.

11. A system according to claim 9, wherein the roller balls are used to provide flexibility of movement for the probe cylindrical base within the cylindrical probe housing during angulations using electromotive force or manual handle.

12. A system according to claim 11, wherein the electromotive force is used to automatically lock the probe in a position by electromagnetic immobilization of the said roller balls to maintain a constant probe-to-vessel angle.

13. A system for automatic manipulation of a transcranial Doppler probe device designed for placement on a patient's head comprising:
  a bi-temporal probe hanger;
  a cylindrical probe housing mounted on a hole on each arm of the said bi-temporal probe hanger wherein said cylindrical probe housing having an inner electrical wiring and said inner wiring for generating electromotive force for angulations of the probe and for probe position sensing;
  an ultrasound transducer with cable operatively connected to the transcranial Doppler device and affixed on the probe cylindrical base wherein said probe cylindrical base inserted within the said cylindrical probe housing and said probe cylindrical base having a base coil said means to generate induction electromotive force used for angulations of the probe;
  a spring system attached to the said probe cylindrical housing said means to apply a perpendicular force to couple the probe to the skin;
  a system of roller balls within the said cylindrical probe housing said means to provide flexibility of movement to the probe cylindrical base;
  an intelligent system software that 'learns' the different possibilities for probe angulations;
  a microprocessor for control of probe position and operatively connected to the transcranial Doppler device and inner wiring of the cylindrical probe housing and coil at the probe cylindrical base; and
  a handle attached to the said probe cylindrical base said means for manually providing angulations of the probe.

14. A system according to claim 13, wherein the electromotive force values in each set of wires are used by neural network system to design membership functions for fuzzy system that are employed for decision-making algorithms for controlling the probe position.

15. A system according the claim 14, wherein the neural network's internal connections and synaptic weights are in turn initialized using the knowledge of the fuzzy logic system.

16. A system according to claim 15, wherein the neural network learns the probe angulations by back propagation learning and changes its symbolic representation accordingly for use in the neural-fuzzy system.

17. A system according to claim 16, wherein the neural-fuzzy system learns the probe angulations by control rules constructed using the acquired knowledge during manual manipulation of the probe cylindrical base.

18. A system according to claim 17, wherein the neural-fuzzy system performs probe-to-vessel angle correction using its knowledge base acquired during insonation independent of an operator.

19. A system and method for transcranial Doppler insonation device for placement on a patient's head comprising:
  a bi-temporal probe hanger;
  a cylindrical probe housing mounted on a hole on each arm of the said bi-temporal probe hanger wherein said cylindrical probe housing having an inner electrical wiring and said inner wiring for generating electromotive force for angulations of the probe and for probe position sensing;
  an ultrasound transducer with cable operatively connected to the transcranial Doppler device and affixed on the probe cylindrical base wherein said probe cylindrical base inserted within the said cylindrical probe housing and said probe cylindrical base having a base coil said means to generate induction electromotive force used for angulations of the probe;
  a spring system attached to the said probe cylindrical housing said means to apply a perpendicular force to couple the probe to the skin;
  a system of roller balls within the said cylindrical probe housing said means to provide flexibility of movement to the probe cylindrical base;
  an intelligent system software that 'learns' the different possibilities for probe angulations;
  a microprocessor for control of probe position and operatively connected to the inner wiring of the cylindrical probe housing and coil at the probe cylindrical base; and
  a handle attached to the said probe cylindrical base said means for manually providing angulations of the probe;
  whereby the bi-temporal probe hanger, cylindrical probe housing, the transducer on the probe cylindrical base with transducer cable are placed using a specified procedure and methodology starting with identifying an temporal acoustic window above an zygomatic arch and placing an ultrasound gel substance on the skin covering the temporal acoustic window, then the bi-temporal probe hanger is placed on the head with center arm positioned in the center of the head and the side arms on the temporal bones from both sides with base on an mastoid process and zygomatic arch and an ear pouch placed around the ear lobe, then the cylindrical probe housing is centered and attached to the hole on the bi-temporal probe hanger using a locking system to mount the said cylindrical probe housing to the frame of the hanger so the it is adjacent to the temporal acoustic window, and placing the probe cylindrical base in the middle so as to allow manual insonation of the cerebral vessels using the detachable handle for steering the ultrasound transducer with the spring and roller ball systems allowing both coupling to the skin by application of perpendicular force and flexibility of movement of the probe cylindrical base respectively until the desired Doppler signals are obtained and the relevant parameters saved, there after the handle is detached, and the system uses the saved parameters to 'learn' and then to maintain probe position using electromotive force and subsequently activating the saved parameters for the same patient during subsequent insonation.

20. A system and method according to claim 19, whereby the learning for automatic self-regulation and repositioning in case of motion artifacts is accomplished using an artificial intelligent software program.

* * * * *